United States Patent [19]

Legros et al.

[11] Patent Number: 5,211,955
[45] Date of Patent: May 18, 1993

[54] PHARMACEUTICAL COMPOSITION CONTAINING A HYDROPHILIC ACTIVE COMPOUND, TREATED WITH AN ORGANIC ACID AND ENCAPSULATED IN A LIPOSOME

[76] Inventors: Franz Legros, rue de Plagniau 8, B-1330 Rixensart; Claude-Pascal Leroy, rue de la Follie 2, B-7190 Ecaussinnes, both of Belgium

[21] Appl. No.: 659,286
[22] PCT Filed: Oct. 12, 1989
[86] PCT No.: PCT/BE89/00047
§ 371 Date: Apr. 10, 1991
§ 102(e) Date: Apr. 10, 1991
[87] PCT Pub. No.: WO90/03781
PCT Pub. Date: Apr. 19, 1990

[30] Foreign Application Priority Data

Oct. 12, 1988 [BE] Belgium ............... 8801180

[51] Int. Cl.$^5$ ............................. A61K 9/127
[52] U.S. Cl. .................... 424/450; 424/427; 264/41; 514/912; 514/39
[58] Field of Search ............... 536/13.6; 424/450, 427, 424/45; 428/402.2; 264/4.1, 4.3, 4.6; 514/912-914

[56] References Cited

U.S. PATENT DOCUMENTS

| | | | |
|---|---|---|---|
| 3,959,255 | 5/1976 | Chazan et al. | 536/13.6 X |
| 3,981,861 | 9/1976 | Chazan et al. | 536/13.6 X |
| 4,242,331 | 12/1980 | Gasc et al. | 536/13.6 X |
| 4,424,344 | 1/1984 | Kirst et al. | 536/13.6 X |
| 4,424,345 | 1/1984 | Kirst et al. | 536/13.6 X |
| 4,468,512 | 8/1984 | Kirst et al. | 536/13.6 X |
| 4,708,861 | 11/1987 | Popescu et al. | 424/458 X |

FOREIGN PATENT DOCUMENTS

| | | |
|---|---|---|
| 0211647 | 2/1987 | European Pat. Off. . |
| 8700043 | 1/1987 | World Int. Prop. O. . |
| 8804573 | 6/1988 | World Int. Prop. O. . |

OTHER PUBLICATIONS

Journal of Controlled Release; vol. 5, No. 2, Sep. 1987 pp. 187–192.
Chemical Abstracts, 101:43477g 1984.

*Primary Examiner*—Thurman K. Page
*Assistant Examiner*—G. S. Kishoke
*Attorney, Agent, or Firm*—Chilton, Alix & Van Kirk

[57] ABSTRACT

A pharmaceutical composition containing an hydrophilic aminoglucoside antibiotic coupled with an organic acid. The coupled aminoglucoside antibiotic and organic acid are encapsulated in a liposome. The composition of the invention is self-regulating in that it liberates the active compound in inverse proportion to the concentration of the compound in the external medium. As a result, the composition serves as a long-acting antibiotic while avoiding the release of a toxic or ineffective dose of the antibiotic into the subject.

20 Claims, 4 Drawing Sheets

PHARMACEUTICAL COMPOSITION CONTAINING A HYDROPHILIC ACTIVE COMPOUND, TREATED WITH AN ORGANIC ACID AND ENCAPSULATED IN A LIPOSOME

SUBJECT OF THE INVENTION

The present invention relates to a pharmaceutical composition containing a hydrophilic active compound treated with an organic acid so as to achieve the formation of a complex between the two molecules, and encapsulated in a liposome.

SUMMARY OF THE STATE OF THE ART

Numerous substances exhibit pharmacological properties but are not used to their optimum efficiency because they do not possess all the properties of a good pharmaceutical compound. To remedy the insufficently potent action of these medicaments by increasing the doses would lead to an undoubted toxicity. Thus, if in order to remedy an excessively weak or excessively short-lasting action, a higher dose of active compound is injected, this runs the risk of causing high toxicity or secondary effects (which may be allergic, digestive, renal, nervous, hematological or the like). Specifically, the nephrotoxicity, ototoxicity and neurotoxicity of gentamycin and of the other aminoglucoside antibiotics have been extensively described.

Furthermore, publications on the encapsulation of antibiotics such as gentamycin (Morgan, J. R. and Williams, K. E., 1980, Antimicrob. Agents Chemother. 17: 544–548; Barza, M., Baum, J. and Szoka, F., 1984, Invest. Ophtalmol. Vis. Sci. 25:486–490) show that the authors only achieved degrees of encapsulation of between 5% and 25%.

Other publications (WO-Al-88/04573, The Liposome Company; WO-Al-87/00043, The Liposome Company; Schreier, H. and coll., 1987, J. Controlled Release 5: 187–192) refer only to the use of inorganic molecules in techniques for the encapsulation of antibiotics.

A use of organic acids for the preparation of a gel consisting of dehydrated liposomes is known from a European patent (EP-Al-0211647), but without coupling to the pharmaceutical molecules, and at much higher pH values than those of the encapsulated molecules. The organic acid is only used for the rehydration of the liposomes.

OBJECTS OF THE INVENTION

The present invention proposes to provide a product which, after encapsulation, :as the valuable property of being self-regulating, in &he sense that it liberates the active compound in inverse proportion to the concentration of this compound in the external medium. This has the advantage of guaranteeing a sustained action of the administered antibiotics, whilst avoiding giving rise to toxic doses or ineffective doses.

These properties are particularly valuable for certain applications, especially ophthalmological applications, which will be described below and for which the presence of an active compound in excessively high concentration can cause irreversible lesions. Additionally, the product of the invention also exhibits high degrees of encapsulation which can reach 50%.

CHARACTERISTIC ASPECTS OF THE INVENTION

In order to achieve the objects thus sought, the invention proposes a pharmaceutical composition containing a hydrophilic active compound treated with an organic acid so as to bring about the coupling of the two molecules, and encapsulated in a liposome. This composition may be characterized by a maximum intraliposomial volume when the hydrophilic active compound is linked to the carboxyl group or groups of the acid. Among the hydrophilic active compounds, the aminoglucoside antibiotics are preferred.

By an aminoglucoside antibiotic there is understood a molecule which comprises glycidyl residues which comprise $NH_2$ groups in a side chain. The term thus encompasses other molecules than those which correspond to the conventional pharmacological definition of so-called aminoglucoside antibiotics.

In particular, gentamycin is treated with an organic acid at a pH of the order of 4.5.

Among the organic acids, preference is given to the amino acids, in particular glutamic acid, or to polycarboxylic acids such as succinic acid or citric acid.

However, monocarboxylic or simple acids such as acetic acid or formic acid may also be suitable.

Preferably, the liposomes employed are of the so-called "multilamellar" (MLV) type with cholesterol.

According to the invention, preference is generally given to multilamellar liposomes with cholesterol which have molar ratios Egg Pc/Chol of between 4/1 and 4/6, this latter ratio or values close thereto being very particularly preferred.

The invention also proposes a process for obtaining the product by carrying out a direct encapsulation of the hydrophilic active compound, that is to say the hydrophilic active compound is brought into contact with the acid and is encapsulated, with formation of a liposome.

The product of the invention is of considerable value because it is found that the encapsulated active principle is liberated in inverse ratio to the presence thereof in the external medium. Applications may be local or systemic and the liposome can be so as to obtain complementary effects such as a targeting in accordance with the tropism of the liposome. Loaded application forms of the liposome can be used, especially in order to cause preferential deposition on a membrane or a tissue.

The preferred presentation of the product of the invention is in the form of a liposomial suspension at a pH of between 4.5 and 7.5.

Such a preparation, after readjustment, if necessary, to the physiological pH, can be applied parenterally or as an aerosol, and oral administration can be envisaged though compounds such as gentamycin are not normally absorbed.

Advantageously, the products of the invention are also used for the preparation of a medicament for local application, especially for opthalmological application.

DESCRIPTION OF A PREFERRED FORM OF THE INVENTION

Figure 1A:
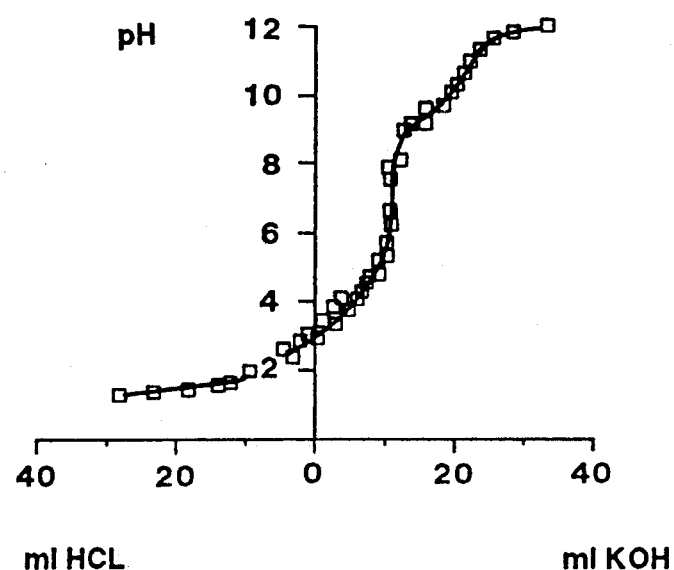
FIG. 1a shows pH values for an acid-base titration of 0.998M glutamic acid with 0.101M KOH and 0.999M HCl.
Figure 1B:
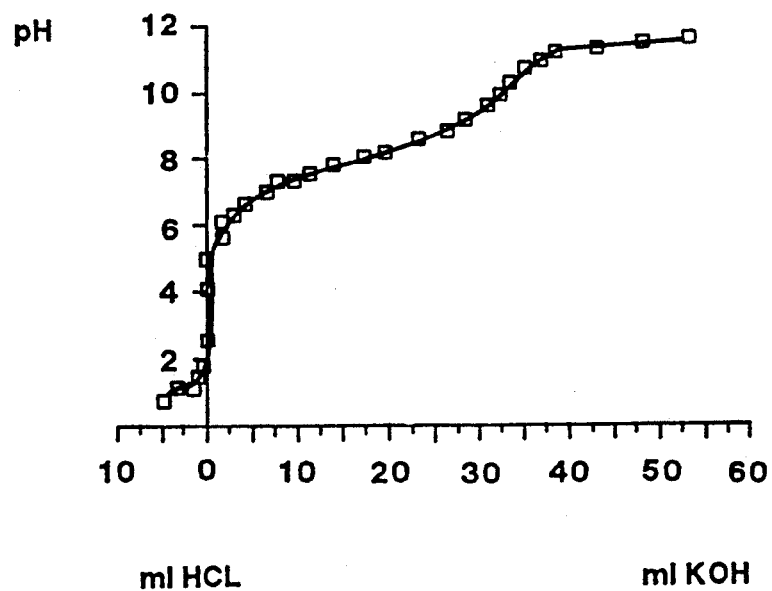
FIG. 1b shows pH values for an acid-base titration of 0.998M sulfated gentamycin with 0.101M KOH and 0.999M HCl.
Figure 1C:
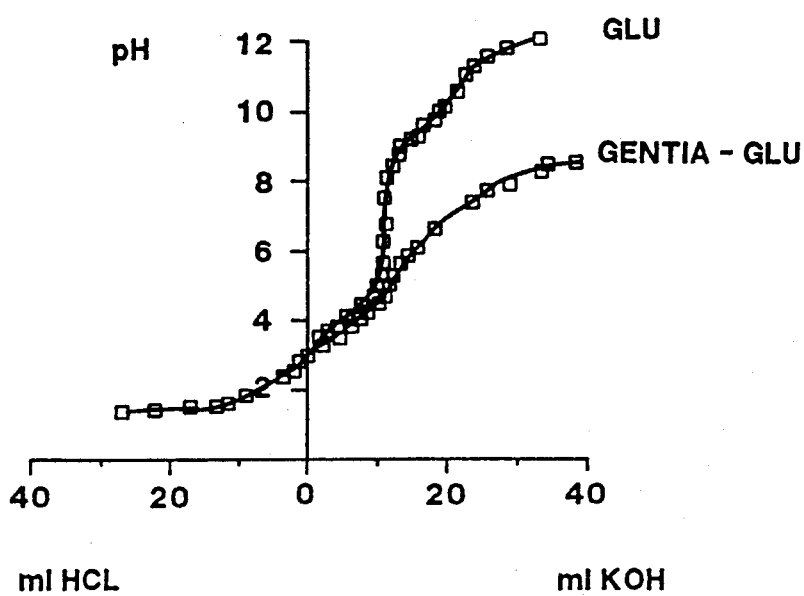
FIG. 1c shows pH values for an acid-base titration of a mixture containing a 1:1 mole ratio of gentamycin and glutamic acid with 0.101M KOH and 0.999M HCl.

The product of the invention is characterized by the combination of a hydrophilic active compound and an organic acid group, or organic acid groups, followed by encapsulation in a liposome.

The product of the invention will be described in greater detail by reference to the tests and the practical examples of carrying out its process of preparation.

Various parameters were successively studied to demonstrate the effect of these on the technique proposed by the invention.

Combination of Gentamycin and Glutamic Acid at pH 4.5

The specific bond between the hydrophilic active compound and the carboxyl groups of the organic acid is characterized by an acid-base titration of the combination of the hydrophilic active compound and the organic acid.

0.998M Glutamic acid was titrated with 0.101M KOH and 0.999M HCl (FIG. Ia). 0.998M Sulfated gentamycin was titrated in accordance with the same procedure (FIG. Ib). The two molecules were then mixed mole for mole and titrated. FIG. Ic shows the disappearance of one of the carboxyl groups of glutamic acid at a pH of the order of 4.5.

Liposomial Encapsulation of Gentamycin in Glutamic Acid

The encapsulation of gentamycin was measured one hour after the formation of the liposomes.

Working Conditions

Liposomial composition: phosphatidylcholine of egg yolk (Egg Pc) and cholesterol (Chol).
Molar ratios of the constituents: 4/3 and 4/6.
Total mass of the lipid constituents: 60 mg.
Amounts of gentamycin: 1, 10 and 20 mg.
Encapsulation volumes: 1, 0.5 and 0.25 ml.
Encapsulation pH: 4.5 and 7.5.
Encapsulation buffer: glutamic acid/KOH (osmolality: 285 mOsm/kg of $H_2O$)

Liposomial Encapsulation Method

Formation of a dry film of Egg Pc and cholesterol;
addition of the mixture of glutamic acid and gentamycin;
suspension of the liposomes by vortexing;
incubation for 1 hour at ambient temperature;
centrifuging at 5000 rpm for 10 minutes;
3 washings of the liposomial pellet with a glutamic acid solution buffered to the same pH as that used for the encapsulation.

The results of the various tests are summarized in Table 1.

TABLE 1

Efficiency of encapsulation (%) of gentamycin mixed with glutamic acid as a function of the pH, of the liposomial composition and of the encapsulation volume.

| pH | mg of gentamycin | molar ratio | volume ml | % encapsulation ± standard deviation | N |
|---|---|---|---|---|---|
| 4.5 | 1 | 4/3 | 1 | 10.5 ± 1 | 24 |
| 4.5 | 1 | 4/3 | 0.5 | 18.2 ± 0.3 | 3 |
| 4.5 | 1 | 4/3 | 0.25 | 21.6 | 1 |
| 4.5 | 1 | 4/3 | 1 | 7.8 ± 0.9 | 3 |
| 7.5 | 1 | 4/3 | 1 | 10.8 ± 1.5 | 26 |
| 4.5 | 1 | 4/6 | 1 | 33.5 ± 3 | 10 |
| 4.5 | 1 | 4/6 | 0.5 | 37.5 ± 5 | 3 |
| 4.5 | 1 | 4/6 | 0.25 | 46.1 | 1 |
| 4.5 | 10 | 4/6 | 1 | 35.4 ± 3.5 | 4 |
| 4.5 | 20 | 4/6 | 1 | 35 ± 3.5 | 8 |
| 7.5 | 1 | 4/6 | 1 | 33.5 ± 3 | 6 |

The efficiency of encapsulation varies from 8 to 46%. The optimum encapsulation was aclieved with liposomes of composition 4/6, at pH 4.5 and in a volume of 0.25 ml.

Influence of the pH of Glutamic Acid on the Efficiency of Encapsulation

Experimental conditions:
Lipid concentration: 60 mg/ml.
Gentamycin concentration: 1 mg/ml.
pH of glutamic acid: 3; 4.5; 7.5.
Incubation time: 1 hour.

Figure 2A:
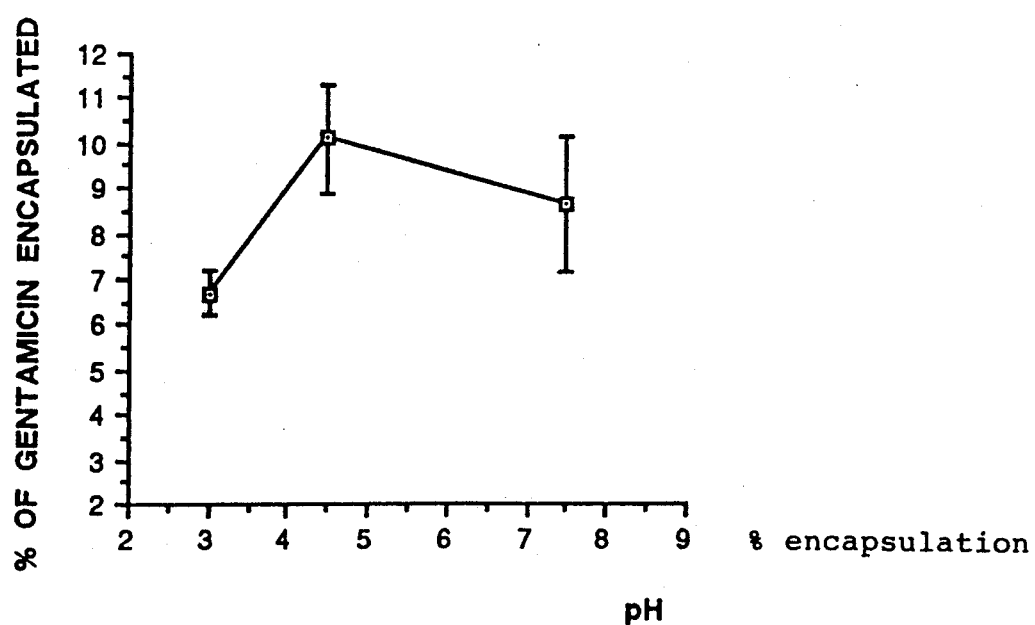
FIG. 2a shows the percentage of gentamycin encapsulation as a function of pH in an encapsulaton buffer of glutamic acid/KOH according to a preferred embodiment of the invention.

The efficiency of encapsulation of the gentamycin increases from pH 3 to 4.5, where it reaches its maximum. At pH 7.5, the efficiency is slightly lower than that measured at pH 4.5 (see FIG. 2a).

Influence of the pH of Glutamic Acid on the Liposomial Volume

The liposomial volume was measured by the encapsulation of inulin labeled with $^{14}C$. The experimental conditions are as follows:
Lipid concentration: 60 mg/ml.
Gentamycin concentration: 20 mg/ml.
pH of glutamic acid: 3; 4.5; 7.5.
pH of the tris-HCl buffer: 7.5.
Incubation time: 1 hour.

Table 2 shows that at pH 7.5, the presence of glutamic acid does not increase the intraliposomial volume relative to tris. In the tris-HCl 7.5 buffer, the addition of gentamycin changes the volume of the liposomes. On the other hand, the addition of gentamycin to glutamic acid at pH 7.5 increases the size of the liposomes more strongly.

TABLE 2

Variation of the intraliposomial volume as a function of the pH and of the composition of the encapsulation medium.

| pH | Liposomes with gentamycin | | Liposomes without gentamycin | |
| --- | --- | --- | --- | --- |
| | glu/KOH | Tris-HCl | glu/KOH | Tris-HCl |
| 4.5 | 176 ± 5 µl | | 90 ± 19 µl | |
| 7.5 | 73.3 ± 1 µl | 67 ± 0.6 µl | 53 ± 3 µl | 54 ± 5 µl |

Figure 2B:
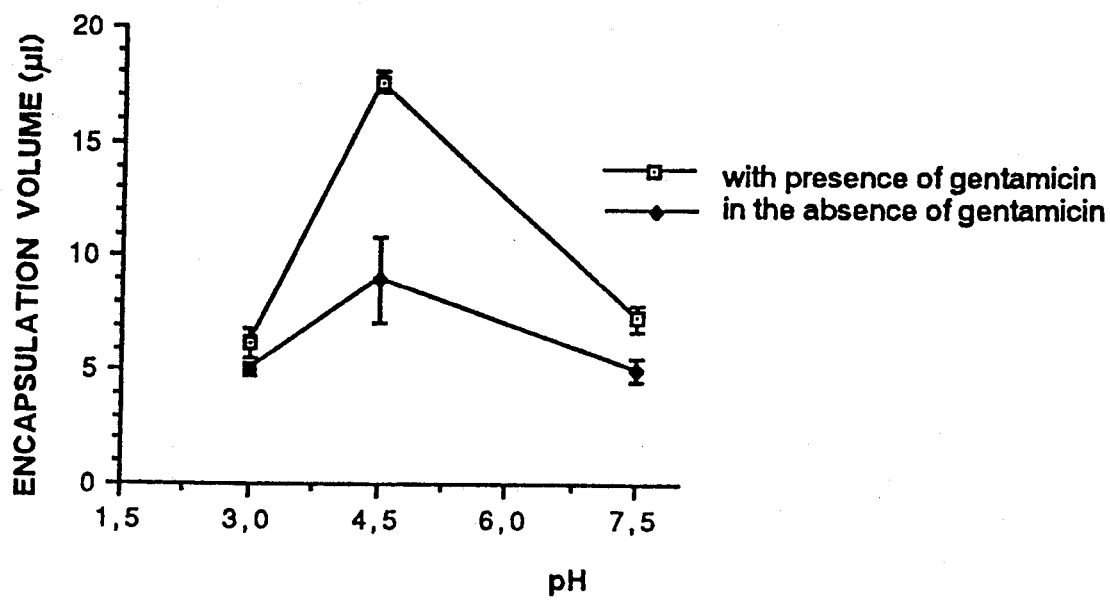
FIG. 2b shows the relationship between intraliposomial volume and pH for liposomes formed according to a preferred embodiment of the invention, with and without the addition of gentamycin to a glutamic acid/KOH buffer.

The addition of gentamycin to glutamic acid used as a buffer increases the liposomial volume at the three pH values. This increase is however much more marked at pH 4.5, where the presence of gentamycin doubles the liposomial volume (Table 2 and FIG. 2b).

Liposomial Encapsulation in other Organic Acids

The encapsulation of gentamycin at pH 4.5 was carried out in succinic acid, acetic acid and formic acid. The encapsulation efficiencies were of the order of those achieved in glutamic acid under the same experimental conditions.

Specifically, encapsulations were carried out in a citrate/acetate buffer used for ophthalmological administration.

TABLE 3

Efficiency of encapsulation (%) of gentamycin mixed with a citrate/acetate buffer, as a function of the pH and of the liposomial composition (60 mg of lipids).

| PH | Concentration of gentamycin mg/ml | Molar ratio | % encapsulation ± standard deviation | N |
| --- | --- | --- | --- | --- |
| 4.5 | 1 | 4/3 | 15.9 ± 6.3 | 3 |
| 7.5 | 1 | 4/3 | 12.5 ± 2.1 | 3 |
| 4.5 | 1 | 4/6 | 34 ± 2.8 | 3 |
| 7.5 | 1 | 4/6 | 35 ± 4.1 | 3 |

Once again, the optimum encapsulation (35%) is achieved when the gentamycin mixed with the buffer, at pH 4.5 or 7.5, is encapsulated in liposomial structures whereof the molar ratio Egg Pc/Chol is 4/6.

Release of the Encapsulated Gentamycin

In order to determine the time for release from the liposomes and the optimum dose of gentamycin liberated after encapsulation at pH 3, 4 5 and 7.5, its kinetics of release were studied in two physiological media:
bovine vitreous humor at pH 7.2, 300 mOsmol/kg of $H_2O$,
rabbit plasma at pH 7.2, 287 mOsmol/kg of $H_2O$.
  The gentamycin liberation takes place at 37° C.
  Experimental conditions:
Lipid concentration: 60 mg/ml.
Gentamycin concentration: 1 mg/ml.
Molar ratio Egg Pc/Chol: 4/3.
pH of encapsulation in glutamic acid: 3; 4.5; 7.5.
  After formation of the liposomes and washing, the liposomial pellet is suspended in 1 ml of vitreous humor or of plasma. The gentamycin remaining in the liposomes is measured at various times.

Figure 3A:
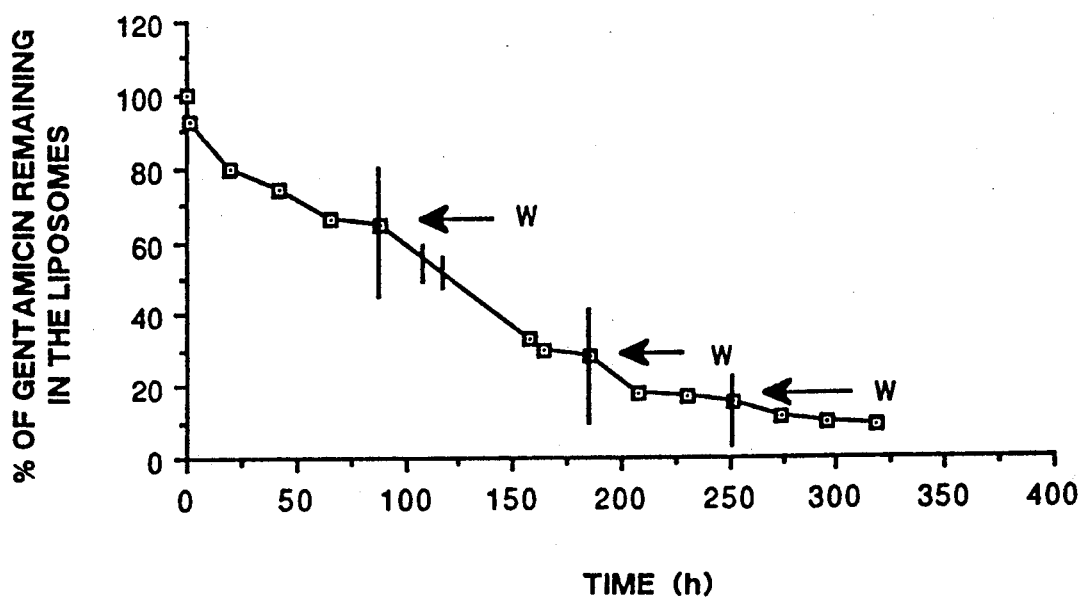
FIG. 3a shows the percentage of gentamycin remaining in a liposome as a function of time when a liposome formed according to a preferred embodiment of the invention at a pH of 4.5 is suspended in rabbit plasma.

Release from Rabbit Plasma (FIG. 3a)

The release of gentamycin from the liposomes formed at pH 4.5 in glutamic acid is gradual. When the gentamycin released into the plasma reaches a critical value, the drug ceases to be released from the liposomes. If the plasma is renewed, the release resumes (see the attached FIG. 3a, where W represents &he replacement of the plasma charged with gentamycin by fresh plasma).

After several washes of this type, the liposomes can be completely emptied of the drug. This means that once they have been introduced into the biological liquids, the liposomes can release gradually, in a manner which is retro-controlled by the extraliposomial concentration of gentamycin, the whole of the drug which was encapsulated in them.

Release into the Vitreous Humor

Figure 3B:
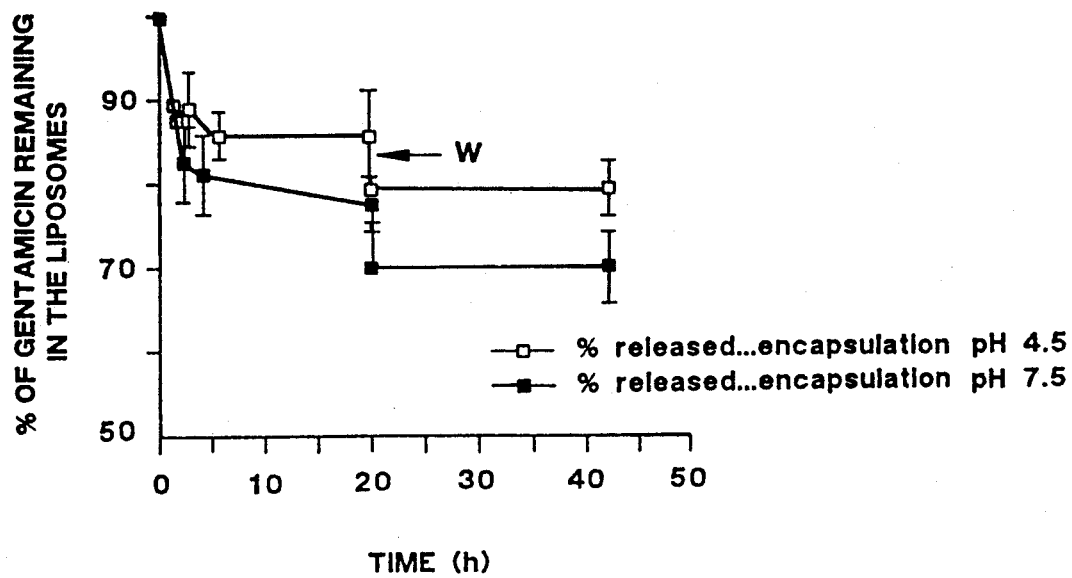
FIG. 3b shows the percentage of gentamycin remaining in a liposome as a function of time when liposomes formed at pH values of 4.5 and 7.5 are suspended in bovine vitreous humor.

If the gentamycin has been encapsulated in glutamic acid buffer at a pH of 4.5 or 7.5, the release of the drug into the vitreous humor takes place in the same manner as into the plasma (FIG. 3b).
Gradual release;
saturation of the vitreous humor;
resumption of release after renewal of the vitreous humor.

The percentage of gentamycin released before the vitreous humor is saturated is greater at pH 7.5 than at pH 4.5. The choice of the pH for encapsulation in glutamic acid thus makes it possible to offer various pharmaceutical forms which possess drug release properties which can meet various clinical requirements.

Figure 3C:
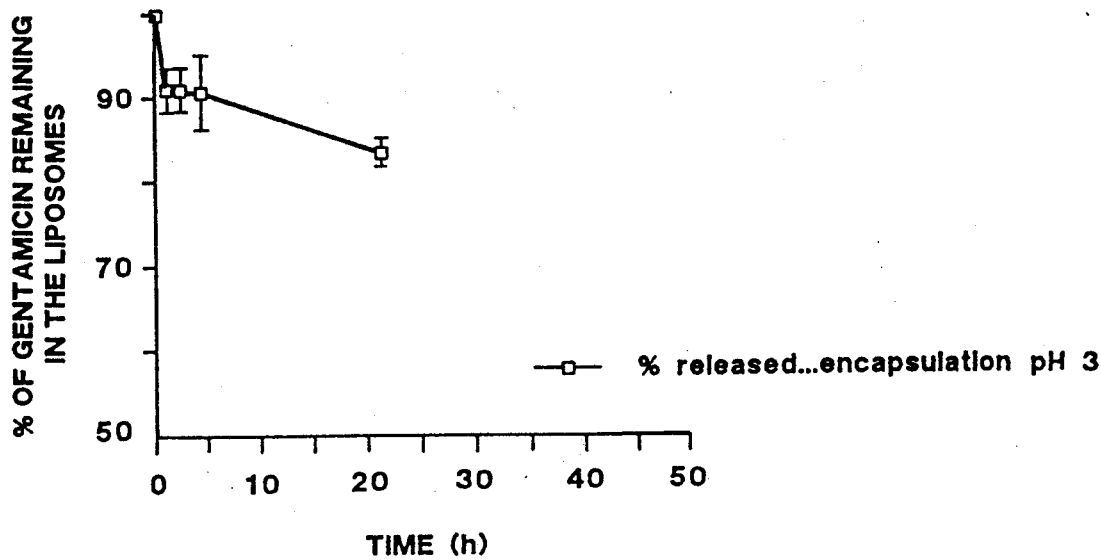
FIG. 3c shows the percentage of gentamycin remaining in a liposome as a function of time for liposomes which are formed at a pH of 3 and are suspended in bovine vitreous humor.

On the other hand, the release of gentamycin encapsulated in glutamic acid at pH 3 does not exhibit this form of retro-control by the concentration of the drug in the physiological medium. The release of the drug takes place continuously (FIG. 3c).

Release of Gentamycin into Rabbit Vitreous Humor in Vivo

Experimental conditions:
Liposomes: 20 mg/ml of gentamycin and 20 mg/ml of lipids (Egg Pc/Chol, molar ratio 4/6); encapsulation time: 1 hour.

0.1 ml of liposomial pellet, containing 1 milligram of gentamycin, is injected into the vitreous humor of the anesthetized rabbit.

The rabbits are sacrificed after 24 and 48 hours and the vitreous humor is removed.

The humor is centrifuged (5000 rpm, 20 minutes), the liposomial pellet and the humor are separated and the amount of gentamycin in the two fractions is measured.

The results are expressed as the ratio of the amount of gentamycin liberated into the vitreous humor to the amount remaining in the liposomes (Table 4).

TABLE 4

Release of gentamycin into the vitreous humor in vivo

| Rabbits | Times | Ratio supernatant liquor/pellet |
| --- | --- | --- |
| No. 1 | 24 h | 7.79% |
| No. 2 | 24 h | 6.26% |
| No. 3 | 48 h | 6.83% |
| No. 4 | 48 h | 5.09% |

From 24 to 48 hours after the injection, the ratio remains constant. This indicates the existence of a slow and constant release of the gentamycin into the biological liquids in vivo.

We claim:
1. Pharmaceutical composition containing an hydrophilic aminoglucoside antibiotic coupled with an organic acid, the coupled aminoglucoside antibiotic and organic acid being encapsulated in a liposome.

2. Pharmaceutical composition according to claim 1, wherein the aminoglucoside antibiotic is sulphated gentamycin which is treated with an organic acid at a pH of about 4.5 to 7.5.

3. Pharmaceutical composition according to claim 1, wherein the organic acid is selected from the group consisting of amino acids, polycarboxylic acids, and monocarboxylic acids.

4. Pharmaceutical composition according to claim 1, wherein the the liposome is multilamellar.

5. Pharmaceutical composition according to claim 1, wherein the liposome exhibits an Egg Pc/Ch ratio of between about 4/1 and 4/6.

6. Pharmaceutical composition according to claim 2, wherein the sulphated gentamycin is treated with an organic acid at a pH of about 4.5.

7. Pharmaceutical composition according to claim 3, wherein the organic acid is selected from the group consisting of glutamic acid, succinic acid, citric acid, acetic acid and formic acid.

8. Pharmaceutical composition according to claim 4, wherein the liposome contains cholesterol.

9. Pharmaceutical composition according to clam 5, wherein the liposomes has an Egg Pc/Ch ratio of about 4/6.

10. Pharmaceutical composition comprising gentamycin coupled with an organic acid selected from the group consisting of amino acids, polycarboxylic acids, and monocarboxylic acids, the coupled gentamycin and organic acid being encapsulated in a multilamellar liposome containing cholesterol.

11. A pharmaceutical composition according to claim 10, wherein the liposome has an Egg Pc/Ch ratio between about 4/1 and 4/6.

12. A method of treating a subject, comprising administering to the subject a therapeutically effect amount of a liposome-encapsulated hydrophilic aminoglucoside antibiotic, the hydrophilic aminoglucoside antibiotic being conjugated with a organic acid.

13. A method according to claim 12, wherein an ophthalmologic affection is treated.

14. A method according to claim 12, wherein the antibiotic is gentamycin and the organic acid is a member selected from the group consisting of amino acids, polycarboxylic acids and monocarboxylic acids.

15. A method according to claim 12, wherein the liposome is multilameller and comprises cholesterol.

16. Pharmaceutical composition according to claim 3, wherein the monocarboxylic acid is acetic acid or formic acid.

17. Pharmaceutical composition according to claim 10, wherein the monocarboxylic acid is acetic acid or formic acid.

18. Pharmaceutical composition according to claim 14, wherein the monocarboxylic acid is acetic acid or formic acid.

19. Pharmaceutical composition according to claim 2, wherein the organic acid is selected from the group consisting of amino acids, polycarboxcylic acids, and monocarboxylic acids.

20. Pharmaceutical composition according to claim 19, wherein the monocarboxylic acid is acetic acid or formic acid.

* * * * *